United States Patent [19]

Shih et al.

[11] Patent Number: 5,312,619
[45] Date of Patent: May 17, 1994

[54] AQUEOUS STABLE COMPLEX OF A STRONGLY SWELLABLE, MODERATELY CROSSLINKED POLYVINYLPYRROLIDONE AND HYDROGEN PEROXIDE

[75] Inventors: Jenn S. Shih, Paramus; John J. Merianos, Middletown; Terry E. Smith, Morristown; Jui-Chang Chuang, Wayne, all of N.J.

[73] Assignee: ISP Investments Inc., Wilmington, Del.

[21] Appl. No.: 875,951

[22] Filed: Apr. 30, 1992

[51] Int. Cl.$^5$ .............................. A61K 31/79
[52] U.S. Cl. .................. 424/78.25; 514/772.5
[58] Field of Search ............ 514/772.5; 525/123; 524/438; 526/258; 424/78.25

[56] References Cited

U.S. PATENT DOCUMENTS

| | | | |
|---|---|---|---|
| 4,192,827 | 3/1980 | Mueller | 525/123 |
| 5,008,093 | 4/1991 | Merianos | 524/438 |
| 5,073,614 | 12/1991 | Shih | 526/258 |

*Primary Examiner*—Thurman K. Page
*Assistant Examiner*—William E. Benston
*Attorney, Agent, or Firm*—Walter Katz; Marilyn J. Maue; Joshua J. Ward

[57] ABSTRACT

A free-flowing, fine white powder of a substantially aqueous stable complex of a strongly swellable, moderately crosslinked polyvinylpyrrolidone (PVP) having an aqueous gel volume of about 15 to 150 ml/g of PVP and a Brookfield viscosity in 5% aqueous solution of at least about 10,000 cps, and $H_2O_2$, in substantially a 1:1 molar ratio of said constituents.

1 Claim, 1 Drawing Sheet

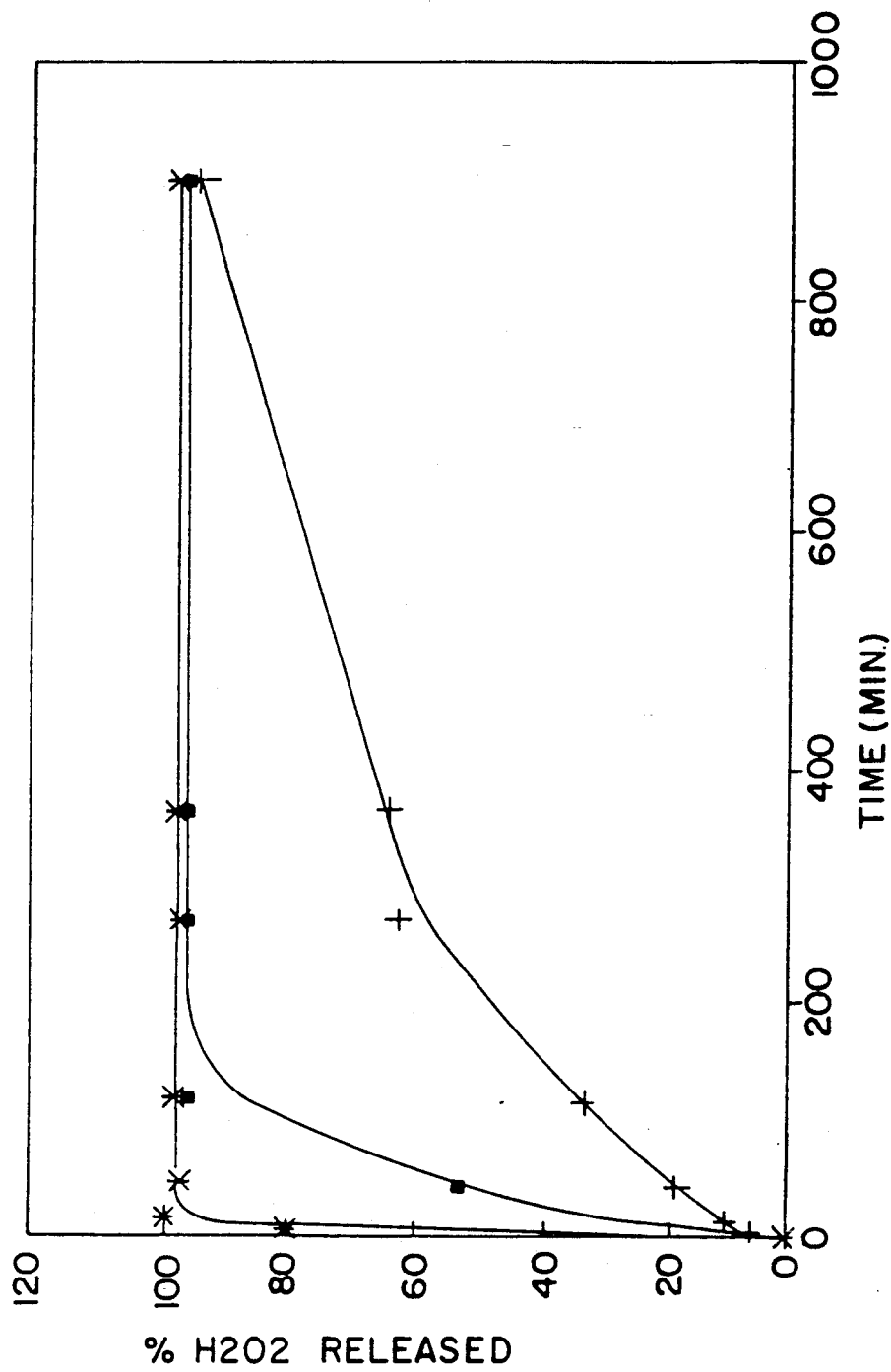

AQUEOUS STABLE COMPLEX OF A STRONGLY SWELLABLE, MODERATELY CROSSLINKED POLYVINYLPYRROLIDONE AND HYDROGEN PEROXIDE

BACKGROUND OF THE INVENTION

1. Field of the Invention

This invention relates to complexes of PVP-$H_2O_2$, and, more particularly, to a complex of a strongly swellable, moderately crosslinked PVP and $H_2O_2$ which is substantially stable in aqueous medium towards decomposition of $H_2O_2$ therein.

2. Description of the Prior Art

Stabilized $H_2O_2$ compositions have found wide utility in commercial and industrial applications, e.g. as antiseptics, disinfectants, sterilization agents, bleaching materials, washing concentrates, etchants, in cosmetic preparations, as cigarette filters, and as a catalyst in polymerizations requiring a free radical source. In biological applications which require an antiseptic, disinfectant or sterilization agent, such $H_2O_2$ compositions require release of an effective amount of oxygen at a desired rate.

The prior art has provided such complexes in various forms. For example Shiraeff, in U.S. Pat. Nos. 3,376,110 and 3,480,557, disclosed that a stabilized hydrogen peroxide composition of hydrogen peroxide and PVP could be prepared by mixing an aqueous solution of PVP and a substantial excess of $H_2O_2$, and evaporating the solution to dryness at 90°-100° C. The $H_2O_2$ content of the composition obtained, however, was quite variable, ranging from 2% to 70% by weight, and considerable water was present in the final composition. Prolonged drying of the composition, in an attempt to reduce its water content, resulted in a further loss of $H_2O_2$. The resultant product was described as a brittle-film, or a transparent, gummy, amorphous material, which lost a considerable portion of its $H_2O_2$ content upon standing, or in aqueous solution.

Merianos, in U.S. Pat. No. 5,008,093, provided free-flowing, stable, high purity, substantially anhydrous complexes of linear (water-soluble) and crosslinked (water-insoluble) PVP and $H_2O_2$ in defined molar ratios of 1:1 or 2:1. These free-flowing products were made by reacting a suspension of PVP and a solution of $H_2O_2$ in an anhydrous organic solvent, such as ethyl acetate. The free-flowing PVP-$H_2O_2$ powders made by Merianos represented a significant advance in this art because its peroxide content was reproducible and the complex in this form could be processed easily into pharmaceutical formulations. However, the process could not be scaled up easily for commercial manufacture of the product.

Biss, in U.S. Pat. No. 5,077,047, described a commercial process for the production of such linear (water-soluble) and crosslinked (water-insoluble) PVP-$H_2O_2$ complexes in the form of free-flowing powders. In the Biss process, a fluidized bed of the PVP powder was maintained at a reaction temperature of from ambient to 60° C. Then the PVP bed was contacted with finely-divided droplets of an aqueous $H_2O_2$ solution containing about 30 to 85% by weight hydrogen peroxide. The resultant product was a stable, substantially anhydrous, free-flowing powder of such PVP-$H_2O_2$ complexes having a 1:1 molar ratio of its components.

Shih, in U.S. Pat. No. 5,073,614, described the preparation of strongly swellable, moderately crosslinked PVP having a predetermined aqueous swelling parameter and a defined viscosity which had effective thickener and gelling properties.

Accordingly, it is an object of the present invention to provide an aqueous stable PVP-$H_2O_2$ product which has gelling and thickening properties in solution.

Another object of this invention is to provide an aqueous stable complex of PVP-$H_2O_2$ having a 1:1 molar ratio of components, the PVP being strongly swellable and moderately crosslinked, as defined by characteristic aqueous swelling and viscosity parameters. These and other objects and features of the invention will be made apparent from the following more particular description thereof.

SUMMARY OF THE INVENTION

A free-flowing, fine white powder of a substantially aqueous stable complex of a strongly swellable, moderately crosslinked PVP having an aqueous gel volume of about 15 to 150 ml/g of PVP and a Brookfield viscosity in 5% aqueous solution of at least about 10,000 cps, and $H_2O_2$, in substantially a 1:1 molar ratio of said constituents.

IN THE DRAWINGS

The FIGURE is a graphical representation of % $H_2O_2$ released with time for tablets of the complex of the invention in water compared with related complexes.

DETAILED DESCRIPTION OF THE INVENTION

U.S. Pat. No. 5,073,614 described strongly swellable, moderately crosslinked PVP polymers in the form of fine, white powders having (a) an aqueous gel volume of about 15 to 150 ml/g of polymer, (b) a Brookfield viscosity in 5% aqueous solution of at least about 10,000 cps, suitably, such polymers are prepared directly by precipitation polymerization of VP in the presence of a crosslinking agent in the amount of about 0.2 to about 1% by weight of VP, as described in U.S. Pat. No. 5,073,614.

In the preferred embodiment of this polymer, (a) is 25 to 75 ml/g of polymer, (b) is at least 15,000 cps, and (c) is about 0.25 to 0.8%. In an optimum form of the invention, (a) is 30 to 60 ml/g, (b) is about 20,000 to 50,000 cps, and, the amount of crosslinker is about 0.35 to 0.6%.

Gel volume is a measure of the swelling property of the crosslinked polymer and is defined as the equilibrium aqueous swelling volume of polymer per unit weight, and is expressed in the units of ml/g. Gel volume is determined by first adding 1 g. of the polymer to a suitable graduated cylinder filled with water. This mixture then is shaken and allowed to stand at room temperature for 3 days. The volume of the gel which is produced in water is measured and taken as the gel volume. Similarly, the gel volume concept can be applied to non-aqueous systems.

Most preferably, the fine, white powder PVP polymers are prepared directly by a precipitation polymerization process in an organic solvent, such as an aliphatic hydrocarbon solvent, preferably cyclohexane or heptane, or an aromatic hydrocarbon, such as toluene, in the presence of about 0.2 to 1% by weight of VP of a crosslinking agent, preferably N,N'-divinylimidazolidone, triallyl-1,3,5-triazine-2,4,6(1H, 3H,5H)-trione 2,4,6-triallyloxy-1,3,5-triazine, or pentaerythritol triallyl ether, at about 10 to 50% solids, preferably 15–30% solids, in the reaction mixture.

The complex of strongly swellable, moderately crosslinked PVP and $H_2O_2$ may be prepared by the methods described in U.S. Pat. Nos. 5,008,093 and 5,077,047.

The invention will now be described in more detail by reference to the following examples.

Preparation of Strongly Swellable, Moderately Crosslinked PVP

EXAMPLE 1

A 2-liter, 4-necked reaction vessel was equipped with a condenser, a constant speed mechanical stirrer, set at 170 rpm with a torque indicator and an anchor agitator having an open radius of 4 and 5/6 inches, an adaptor for admitting nitrogen, and a thermocouple connected to a temperature controller. The vessel was charged with 1000 g. of cyclohexane and heated to 65° C. during 30 minutes while purging with nitrogen. The reactor then was held at 65° C. for an additional 30 minutes. Then 520 microliters of t-butylperoxy pivalate (Lupersol 11, 75% active) polymerization indicator was added. Thereafter a solution of 250 g. of vinylpyrrolidone and 1.25 g. of N,N'-divinylimidazolidone crosslinking agent was introduced into the charged reactor over a period of 4 hours while stirring the contents. The feeding rate was about 1.0 ml./min. Then the mixture was heated to 85° C. over a half-hour and held at that temperature for another half-hour. Then the mixture was transferred to a 2-liter high pressure reactor and 1.0 g. of 2,5-dimethyl-2,6-di-(t-butylperoxy)hexane (Lupersol 101, 90% active) was added. The reactor was sealed and heated to 130° C. for 8 hours, cooled to room temperature, and the mixture was dried in a rotary evaporator. The polymer product was oven dried at 100° C. and vacuum dried at 90° C. for 16 hours of each. A quantitative yield of a crosslinked PVP polymer containing about 0.5% crosslinking agent was obtained. The VP monomer content was 0.01%.

EXAMPLES 2–10

The procedure of Example 1 was followed using various amounts of different crosslinkers with the following results.

TABLE I

| Ex. No. | VP, Amount (g) | Crosslinker* | Crosslinker, Amount (g) | % Crosslinker | **Product Yield (%) |
|---|---|---|---|---|---|
| 2 | 250 | DI | 0.25 | 0.10 | 96.0 |
| 3 | 250 | DI | 0.625 | 0.25 | 100.0 |
| 4 | 250 | DI | 2.5 | 1.00 | 100.0 |
| 5 | 250 | PTE | 0.25 | 0.10 | 93.0 |
| 6 | 250 | PTE | 0.625 | 0.25 | 92.0 |
| 7 | 250 | PTE | 2.5 | 1.00 | 94.2 |
| 8 | 250 | MBA | 0.625 | 0.25 | 87.0 |
| 9 | 250 | MBA | 1.25 | 0.50 | 96.0 |
| 10 | 250 | MBA | 2.5 | 1.00 | 100.0 |

*DI = divinylimidazolidone, PTE = pentaerythritol triallyl ether and MBA = methylene bisacrylamide
**based upon VP used, by weight

EXAMPLES 11–12

The procedure of Example 1 was followed using heptane as solvent in place of cyclohexane. The feeding rate of the solution of vinylpyrrolidone in crosslinking agent was 0.50–0.55 ml./min. The results are shown in Table II below.

TABLE II

| Ex. No. | VP, Amount (g) | Crosslinker | Amount (g) | % Crosslinker | Product Yield (%) |
|---|---|---|---|---|---|
| 11 | 200 | DI | 1.0 | 0.50 | 95.6 |
| 12 | 250 | PTE | 1.25 | 0.50 | 91.5 |

DI - Divinylimidazolidone
PTE - Pentaerythritol triallylether

EXAMPLE 13

The reactor of Example 1 was provided with the anchor agitator positioned in the middle of the reactor and extended to within 2 inches of the bottom of the reactor. Two dip tubes were connected to two metering pumps. The thus-equipped reactor then was charged with the solvent which filled the reactor to about 4 inches above the bottom of the dip tubes. In this procedure, the solution of VP and crosslinking agent was admitted into the reactor through the dip tubes to a position below the surface of the solvent. The effect of such subsurface feeding of monomer-crosslinker solution was to reduce build-up of viscosity of the polymer product during the polymerization, resulting in a smoother course for the process, particularly with respect to effective stirring of the reaction mixture.

Properties of PVP Polymer of Examples 1–13

EXAMPLE 14

The strongly swellable, moderately crosslinked PVP polymer powders of Examples 1–13 are characterized by its unique gel volume and viscosity, which properties enable the polymer to thicken aqueous and non-aqueous solutions effectively.

The viscosity of the polymer is defined by its Brookfield viscosity in cps, which is determined upon a 5% aqueous solution of the polymer at 25° C. by a standard analytical procedure using Model LTV and Spindle No. 4.

For maximum utility, it is desirable that the hydrated polymer exhibit a high gel volume and a high viscosity. With increasing crosslinking density in the polymer, the gel volume decreases and viscosity increases and then decreases, passing through a maximum. In the crosslinked polymer system of this invention, an effective thickener product is provided by including crosslinker in the reaction mixture at a suitable concentration of about 0.2 to 1.0 % by weight, based upon VP, preferably about 0.25 to 0.8%, and optimally, at about 0.35 to 0.6%. At this suitable amount of crosslinker loading, the crosslinked polymer product exhibits a gel volume of about 15 to 150 ml/g of polymer and a Brookfield viscosity of at least 10,000 cps. At the preferred crosslinker concentration, the gel volume is about 25 to 75 ml/g of polymer and its Brookfield viscosity is at least 15,000 cps. At the optimal amount crosslinker present in the reaction mixture, the polymer exhibits a gel volume of about 30 to 60 ml/g of polymer and a Brookfield viscosity of about 20,000 to 50,000 cps.

The viscosity of the crosslinked polymer of the invention is particularly substantially independent of extended storage time even at 50° C., and of pH, and is tolerant of monovalent and multivalent salts in solution.

As an added feature of the invention, the residual VP monomer content of the polymers obtained herein is less than about 0.1% by weight. In aqueous based processes, in contrast, the formation of a gel mass during polymerization may trap considerable amounts of VP monomer in the polymeric gel network.

Preparation of Strongly Swellable, Moderately Crosslinked PVP-$H_2O_2$ Complex

EXAMPLE 15

170 g. of the strongly swellable, moderately crosslinked PVP polymer as made in Examples 1-13 having a particle size of 20-200 microns and a moisture content 1-3%, was introduced into a 22-1 fluidized bed dryer and fluidized at 35°-40° C. using a dry air stream. Then 85 g. of a 50% aqueous solution of $H_2O_2$ was added slowly at a rate of a 5 cc/minute. The resulting product was dried in a vacuum oven at 50° C. to provide a free-flowing, white powder. The yield was 210 g. of the desired complex containing 18.5% $H_2O_2$.

EXAMPLE 16

200 g. of the PVP polymer as made Examples 1-13 was suspended in 600 ml of ethyl acetate and 100 g. of a 70% aqueous $H_2O_2$ solution was added slowly with cooling at 10° C. The resulting product was filtered and dried in a vacuum oven at 50° C. for about 6 hours to provide 256 g. of the desired complex containing 19.4% $H_2O_2$.

Preparation of Stable Aqueous Gel of the PVP-$H_2O_2$ Complex of Invention

EXAMPLE 17

25 g. of the PVP polymer as made in Examples 1-13 was added slowly to 250 ml of water containing 50 g. of 50% $H_2O_2$. The mixture was stirred while an additional 250 ml of water was added. The resulting aqueous gel contained 8.7% PVP-$H_2O_2$ (5.2% available $H_2O_2$ in the gel solution). The viscosity of the gel was 1500 cps.

Comparative Aqueous Stability Properties of Strongly Swellable, Moderately Crosslinked PVP-$H_2O_2$ Products of Invention and PVP-$H_2O_2$ of Prior Art

| Example | Characterization | Wt. Tablet (g) |
| --- | --- | --- |
| 1 | Strongly Swellable, Moderately Crosslinked PVP-$H_2O_2$ | 1.07 |
| U.S. Pat. No. 5,008,093 | Water Soluble PVP-$H_2O_2$ | 0.73 |
| U.S. Pat. No. 5,008,093 | Crosslinked (Crospovidone) Water-Insoluble, PVP-$H_2O_2$ (20% $H_2O_2$) | 0.53 |

The respective samples were tabletted and added to 100 ml of water. Then 10 ml of the aqueous solution was removed periodically and analyzed for % $H_2O_2$ released with time. The results are illustrated graphically in the Figure which demonstrate the particular aqueous stability of the products of the invention as compared complexes made with water soluble or crosslinked (water-insoluble) PVP. The products of the invention also exhibit slow release of $H_2O_2$ with time as compared to a more rapid release initially by the prior art complexes. As gel compositions, the invention complexes herein exhibit excellent thickening properties in both aqueous and organic solutions, which can be utilized in cosmetic personal care, filter and pharmaceutical applications.

While the invention has been described with particular reference to certain embodiments thereof, it will be understood that changes and modifications may be made which are within the skill of the art. Accordingly, it is intended to be bound only by the following claims, in which:

What is claimed is:

1. A gel composition comprising about 5-15% by weight of the reaction product of a strongly swellable, moderately crosslinked PVP powder having an aqueous gel volume of about 15 to 150 ml/g of PVP and a Brookfield viscosity in 5% aqueous solution of at least about 10,000 cps, and $H_2O_2$, in substantially a 1:1 molar ratio of said constituents, and water.

* * * * *